US007665364B2

(12) United States Patent
Su et al.

(10) Patent No.: US 7,665,364 B2
(45) Date of Patent: Feb. 23, 2010

(54) METHOD AND APPARATUS FOR REMOTE SENSING OF MOLECULAR SPECIES AT NANOSCALE UTILIZING A REVERSE PHOTOACOUSTIC EFFECT

(75) Inventors: Ming Su, Oviedo, FL (US); Thomas G. Thundat, Knoxville, TN (US); David Hedden, Lenoir City, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 323 days.

(21) Appl. No.: 11/639,184

(22) Filed: Dec. 14, 2006

(65) Prior Publication Data

US 2007/0220978 A1  Sep. 27, 2007

Related U.S. Application Data (63) Continuation-in-part of application No. 11/386,023, filed on Mar. 21, 2006, now abandoned.

(51) Int. Cl.
G01N 9/24 (2006.01)
A61B 5/00 (2006.01)

(52) U.S. Cl. ............................... 73/643; 73/601; 73/628

(58) Field of Classification Search .................. 73/643, 73/601, 620, 628, 632, 105, 624; 600/309, 600/316, 322, 407, 437–449, 473
See application file for complete search history.

(56) References Cited

U.S. PATENT DOCUMENTS

| 5,042,681 | A | * | 8/1991 | Bolte et al. | .................. | 220/276 |
| 5,544,183 | A | * | 8/1996 | Takeda | .......................... | 372/26 |
| 5,977,538 | A | * | 11/1999 | Unger et al. | .............. | 250/227.2 |
| 6,006,593 | A | * | 12/1999 | Yamanaka | .................... | 73/105 |
| 6,105,431 | A | * | 8/2000 | Duffill et al. | .................. | 73/624 |
| 6,212,921 | B1 | * | 4/2001 | Knighton | ........................ | 70/58 |
| 6,611,332 | B2 | * | 8/2003 | Funakawa | .................... | 356/402 |
| 6,778,564 | B2 | * | 8/2004 | Funakawa | .................... | 372/20 |

(Continued)

FOREIGN PATENT DOCUMENTS

EP  1 346 684 A1  9/2003

(Continued)

*Primary Examiner*—J M Saint Surin
(74) *Attorney, Agent, or Firm*—Boyle Fredrickson, S.C.

(57) ABSTRACT

A method and apparatus for identifying a sample, involves illuminating the sample with light of varying wavelengths, transmitting an acoustic signal against the sample from one portion and receiving a resulting acoustic signal on another portion, detecting a change of phase in the acoustic signal corresponding to the light of varying wavelengths, and analyzing the change of phase in the acoustic signal for the varying wavelengths of illumination to identify the sample. The apparatus has a controlled source for illuminating the sample with light of varying wavelengths, a transmitter for transmitting an acoustic wave, a receiver for receiving the acoustic wave and converting the acoustic wave to an electronic signal, and an electronic circuit for detecting a change of phase in the acoustic wave corresponding to respective ones of the varying wavelengths and outputting the change of phase for the varying wavelengths to allow identification of the sample. The method and apparatus can be used to detect chemical composition or visual features. A transmission mode and a reflection mode of operation are disclosed. The method and apparatus can be applied at nanoscale to detect molecules in a biological sample.

25 Claims, 8 Drawing Sheets

U.S. PATENT DOCUMENTS

| | | | |
|---|---|---|---|
| 6,921,366 B2 * | 7/2005 | Jeon et al. | 600/309 |
| 6,979,292 B2 * | 12/2005 | Kanayama et al. | 600/437 |
| 7,240,541 B2 * | 7/2007 | Niwa et al. | 73/105 |
| 7,363,617 B2 * | 4/2008 | Barsness et al. | 717/129 |

FOREIGN PATENT DOCUMENTS

| | | |
|---|---|---|
| WO | WO 01/17424 A1 | 3/2001 |
| WO | WO 02/15776 A1 | 2/2002 |

* cited by examiner

METHOD AND APPARATUS FOR REMOTE SENSING OF MOLECULAR SPECIES AT NANOSCALE UTILIZING A REVERSE PHOTOACOUSTIC EFFECT

CROSS-REFERENCE TO RELATED APPLICATIONS

This is a continuation-in-part of U.S. patent application Ser. No. 11/386,023 filed Mar. 21, 2006, and now abandoned, and the benefit of an earlier filing date is claimed for the common subject matter.

STATEMENT REGARDING FEDERALLY SPONSORED RESEARCH

This invention was made with Government support under Contract No. DE-AC05-000R22725 awarded to UT-Battelle, LLC, by the U.S. Department of Energy. The Government has certain rights in this invention.

TECHNICAL FIELD

The field of the invention is methods and machines for spectrometry, particularly those methods and machines utilizing both light waves and acoustics.

BACKGROUND ART

An urgent and widespread need exists for the remote sensing and recognition of hazardous chemicals in various field environments. However, current techniques available for such purpose are very limited as compared to that of contact or proximal detections. Existing techniques based on laser detecting and ranging (LADAR) and hyper-spectral imaging are cumbersome, sophisticated and expensive and, therefore, are not ideal for the desired quick and widespread deployment. Meanwhile, some highly light-scattering materials such as amorphous solid, powder, gel and suspension are not readily amenable to the conventional optical detection.

It has been reported that an interaction between electromagnetic radiation in the visible spectrum and a material can be detected photoacoustically or photothermally, where the sample temperature increases as a result of light absorption. In the direct photoacoustic effect, when the sample is illuminated with an intensity-modulated chopped light, an acoustic signal is produced at a certain wavelength due to light absorption by the sample molecules. Unfortunately, the direct photoacoustic method is unsuitable for the remote detection of chemicals as it needs a special resonance chamber to amplify the signal, and further requires that the acoustic transducer be physically very close to the sample.

The local temperature of the sample can also be detected using the so-called mirage effect, where a laser beam is passing over the sample when the sample is illuminated by an incident light. The temperature increase leads to a pressure change in the nearby medium, which in turn deflects the laser beam and is detected. However, the detection of deflected laser beam requires a photodetector at variable positions around the sample, which in some field cases is impossible. Although an infrared camera can detect the temperature of the remote sample, its passive nature makes it sensitive to environment variations. In addition sensitivity and spectral resolution of infrared sensors are not sufficient to detect extremely small variations in temperature in the presence of a background created by an illuminating wavelength. In contrast, active sensors generate their energy with known properties and can be used under a wider range of operational condition with fewer constraints.

Today there is a gap between ranges of scales in which imaging techniques can be used. One range is provided by confocal/multiphoton techniques and another range is provided by x-ray/neutron techniques. As materials and structures of nanoscale become of interest, there is a need to identify and provide images of surface molecules and molecules within biological cells.

Various commercial characterization tools such as force modulation microscopy (FMM), nano-indentation, and picosecond ultrasonic and photoacoustic probes, and confocal microscopes address some aspects of samples. Each tool, however, fails to meet one or more of the key criteria regarding spatial resolution, quantitative capability or nondestructive nature. FMM lacks dynamic range for materials with contact stiffness exceeding the cantilever spring constant and is qualitative. FMM lacks dynamic range for materials with contact stiffness exceeding the cantilever spring constant and is qualitative. Nanoindenters are quantitative, but destructive of the samples being analyzed. Far-field ultrasonic microscopy suffers from spatial resolution limitations. Moreover, all far field microscopes lack: resolution limitations due to Rayleigh limit, coupling fluid attenuation ~f2, and impedance mismatches. Recently, ultrasonic force microscopy has been widely used to map the elastic properties of soft and hard surfaces. It also provides quantitative analysis of surface mechanical properties, but it does not possess sub-surface imaging capabilities and have limited depth resolution of few nanometers.

SUMMARY OF THE INVENTION

The invention is practiced at nanoscale by using a source of light of varying wavelengths to cause heating of molecules in a sample to different temperature, and then applying acoustic signals to the sample which change phase in response to the heating, and then detecting the phase changes, and displaying phase change data in a graph or table, for example, for observing comparisons of results for different molecules.

More particularly, the method of the invention is based on detecting changes in acoustic signals that are produced at different wavelengths of electromagnetic radiation due to absorption sprectra to identify a sample in a reliable fashion. The acoustic signals include an acoustic carrier wave train of pulses and the changes are changes in phase of individual pulses. An electromagnetic radiation source is used to transmit a beam of light at varying wavelengths into the sample which increases the temperature of sample and nearby medium, which in turn changes the phase angle of an ultrasonic wave reflecting from or traveling through the sample. A spectrum of phase change data is obtained in this way, and when analyzed according to methods known in the art, can provide identification of the sample. The identification of the sample can be accomplished within a reasonable degree of certainty for a predetermined number of spectra already known in the art of spectrometry.

This method can be used in a transmission mode or in a reflection mode, but the reflection mode is preferred because it allows a spectrometer to be aimed at a target sample some distance away. Although this method is first disclosed for detecting chemical signatures at measurable distances, it can also be used for detecting chemical signatures where the transducer is in contact with (zero distance from) the sample. An example is the detection of glucose where an acoustic source, an optical source, and the acoustic detectors are in contact with the skin or a body part, such as a tongue, for example.

Compared with direct photoacoustic methods, the method of the present invention does not require a resonance chamber to amplify the signal and can work in both transmission and reflection modes. Generally, the phase spectrum is assumed to have no resemblance to either absorbance or direct photoacoustic spectrum. However, preliminary testing results indicate an evident resemblance between the phase change spectrum and the absorbance spectrum even with low spectral resolution. The resemblance of phase variation as function of wavelengths of illuminating light to that of absorbance spectra will be particularly useful in identifying objects in some specific applications.

An apparatus according to the invention comprises at least one controllable source of electromagnetic radiation, a plurality of filters for filtering the radiation from the source to a specific wavelength and for changing the filters to vary that wavelength that contacts a sample to provide photo-excitation, a transmitter for directing an ultrasonic wave to the sample after the sample has been contacted by the source, and a receiver for receiving the ultrasonic wave after the wave has contacted the sample and an electronic circuit for receiving signals from the receiver and for detecting phase changes resulting from the photo-excitation of the sample at a plurality of wavelengths and providing an output of this phase change. The frequency of the electromagnetic radiation can be in the UV range, the visible spectrum, the near infrared range, the far infrared range, the Mhz range and the Terahertz range. The frequency of the acoustic waves which can be used with the invention includes ultrasonic waves.

The operation of the device involves sensing an acoustic pulse or train of pulses to the sample and getting a reflected acoustic pulse signal and measuring the phase difference between the source and the detector. The process is repeated again while illuminating the sample with a selected wavelength of an electromagnetic wave and noting the phase difference in pulses between the source and the detected acoustic pulse train. This phase difference is an indication of electromagnetic wave absorption by the sample. The process is repeated for many selected wavelengths of the electromagnetic spectrum. The differential phase shift as a function of wavelength shows the absorption spectrum of the sample.

In a further advantageous modification to the above methods, a first acoustic signal can be transmitted to sample and then detected after contacting the sample without illumination by electromagnetic radiation. A phase difference is determined between the first acoustic signal at a source and the first acoustic signal at a detector. A second acoustic signal can then be transmitted to the sample and detected while the sample is being illuminated by electromagnetic radiation. A second phase difference is determined for between the second acoustic signal at a source and the first acoustic signal at a detector. A differential phase difference can then be determined between these two phase differences and in response thereto displaying electromagnetic absorption spectra for the sample. This differential mode of operation eliminates interference due to variation in an intervening medium.

A spectrum of phase change data is obtained in this way, and when analyzed according to methods known in the art, can provide identification of the sample. The identification of the sample can be accomplished within a reasonable degree of certainty for a predetermined number of spectra already known in the art of spectrometry.

Other objectives and advantages of the invention will become apparent from the following description in which reference is made to the drawings, which form a part hereof, and which illustrate one or more preferred embodiments. For the full scope of the embodiments covered by the invention, reference is made to the claims following the description.

DETAILED DESCRIPTION OF THE PREFERRED EMBODIMENTS

Figure 1:
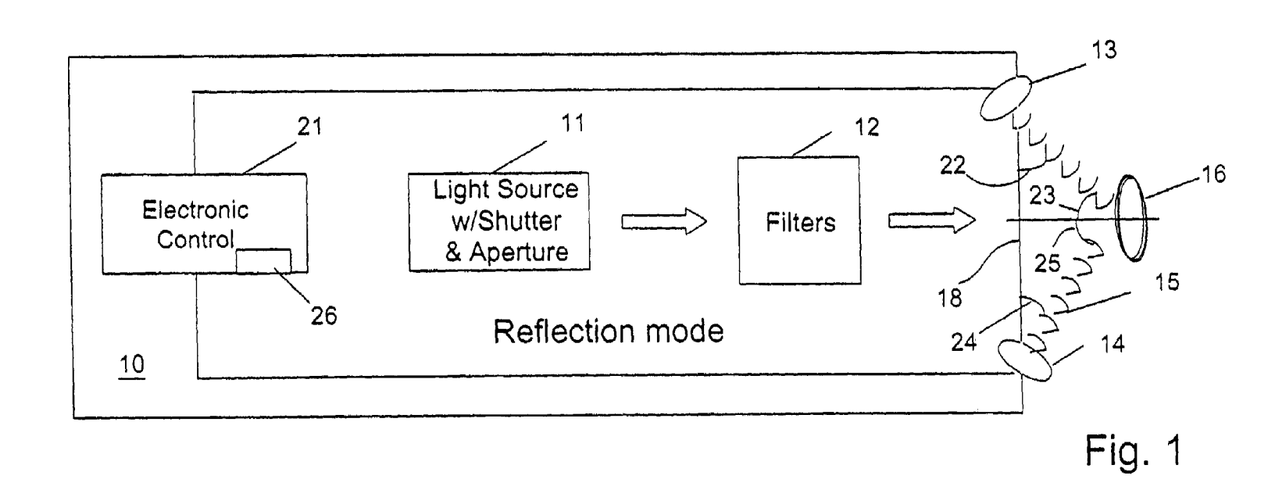
FIG. 1 is a block diagram of an apparatus for practicing the present invention in a reflection mode.
Figure 2:
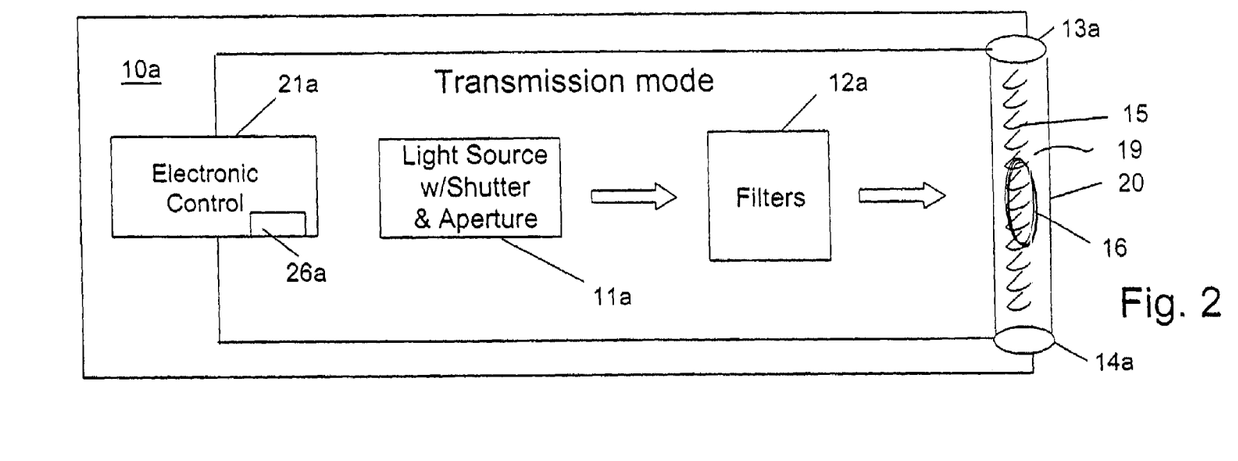
FIG. 2 is the apparatus of FIG. 1 with modifications for practicing the present invention in a transmission mode.

Referring to FIGS. 1 and 2, a machine 10 for practicing the method of the invention at larger than nanoscale has a controllable light source 11 with a shutter and an aperture for controlling a duration and a width of a light beam. The machine 10 is provided with suitable user controls, such as on-off switches and a pushbutton or trigger-operated switch to momentarily apply the light source. One suitable example of a controllable light source 11 for the UV-visible region uses a 300-Watt Xenon lamp and accompanying power supply from Thermal Oriel. The light source 11 can also be a source for producing electromagnetic radiation in the near infrared range, the far infrared range, lasers of different wavelengths, and other tunable sources. A group of interference filters 12 is selectively and successively inserted along the path of the light to allow light with respective narrow wavelength bands to pass (Melles Griot). In test experiments, ethanol solutions of a plurality of dyes are used as adjustable light filters, however, in a machine 10 a plurality of interchangeable colored lenses are preferred. In the dye solutions, dye molecules are selected based on their maximum absorbance wavelength ($\lambda_{max}$) in the range from 370 nm to 800 nm.

The embodiments of FIGS. 1 and 2 each include an ultrasonic transducer/transmitter 13, 13a and an ultrasonic receiver/transducer 14, 14a (ITC Transducer 9040) that have intrinsic frequencies of 40 kHz or 93 kHz, transmit bandwidths of at least 4 kHz, and beam angles of approximately 10 degrees, which shall mean±5 degrees. The narrow acoustic beam 15 shows high directionality that is useful to reach a remotely placed target sample 16. These transducers 13, 13a, 14 and 14a are firmly fixed at a distance 18 of 7 cm to each other and orientated to get maximum ultrasonic signal in the receiving transducer.

In FIG. 1, an acoustic transducer transmitter 13 is aimed to direct a signal to a sample 16 at an angle of ten degrees 22 relative to a straight line path 18 between the transmitter 13 and the receiver 14. The angle is somewhat exaggerated in the drawing for ease of viewing. The angle of incidence 23 of the acoustic wave on the sample is the complement of this angle 22 or approximately eighty degrees. From the sample 16, it is reflected to the transducer/receiver 14, also at an angle 24 of ten degrees from the straight line path 18 between the transmitter 13 and the receiver 14. The angle is somewhat exaggerated in the drawing for ease of viewing. The complement of this angle 24 is an angle of reflection 25 and is approximately eighty degrees. This is the reflection mode and is advantageous if the distance from the machine 10 to the sample can be extended up to several meters or more.

In FIG. 2, the parts corresponding to parts already described for FIG. 1 are denoted by an "a" suffix. The transmitter 13a directs the acoustic wave 15a through a chamber 19 formed in a tubular housing 20 and the acoustic wave 15a is detected at an opposite end of the chamber 19 by receiver 14a. This is the transmission mode in which the sample 16 must be placed in the machine 10. In both cases, the light excitation is transmitted to the sample 16a at an angle that bisects the angle between the transmitter 13, 13a and the receiver 14, 14a, to provide half angles 23, 25 of eighty degrees in FIG. 1, and ninety degrees in FIG. 2 (a non-reflection mode).

An electronic control 21 in the form of an SR-850 digital lock-in amplifier (Stanford research system) is used to drive the vibration of the acoustic transducer transmitters 13, 13a and to collect the reflected or transmitted ultrasonic signals from the acoustic transducer receivers 14, 14a. This electronic control 21, 21a provides a digital display 26, 26a with sonic velocity and phase angle changes of the received signals in comparison with the transmitted signals. It is also contemplated that a personal computer could be connected to receive the velocity and phase angle data from the control 21 and provide visual and graphical displays of the spectral data measured over time and for different filters.

The testing samples, which are in the form of pellets, thin films and gels, are subjected to an ultrasonic wave in a reflection mode seen in FIG. 1 and in a transmission mode seen in FIG. 2. The optical absorbance spectra of the test samples were measured on a Beckman-Coulter DU 530 UV-vis spectrometer, which is a separate piece of equipment and not a part of the machine 10.

Figure 3A:
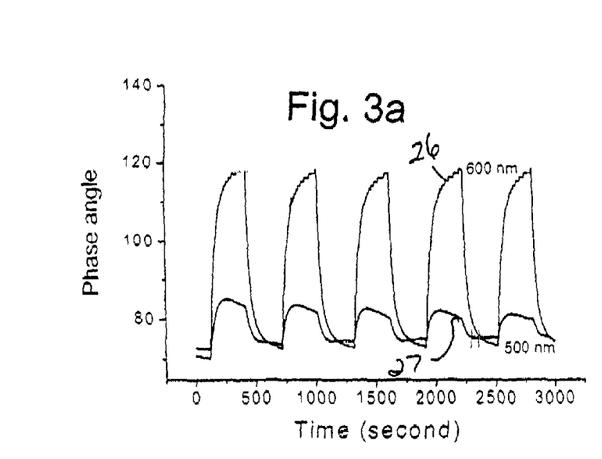
FIG. 3a is a graph of phase angle change as a function of time for a test sample in a transmission mode under illumination using 600 nm and 500 nm interference filters.
Figure 3B:
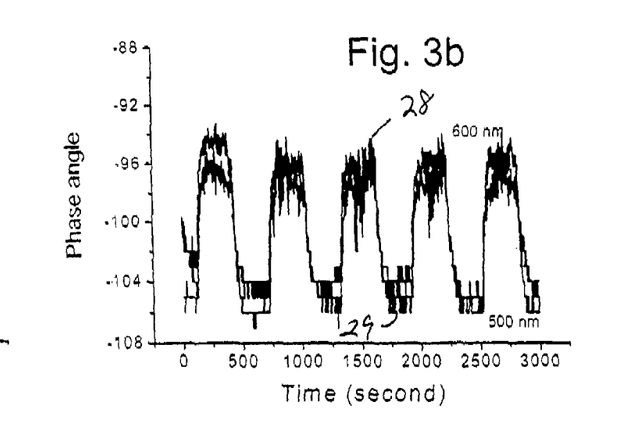
FIG. 3b is a graph of phase angle change for a second test sample in the reflection mode under illumination using 600 nm and 500 nm interference filters.
Figure 3C:
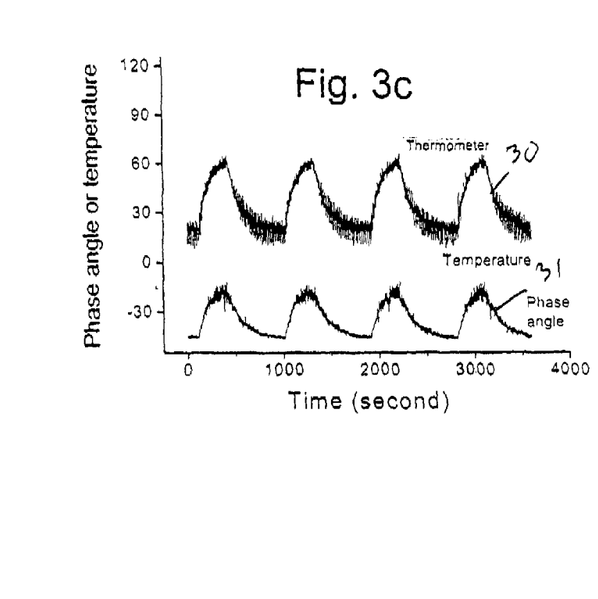
FIG. 3c is a graph of phase angle and temperature of a test sample using a using a dye solution ($\lambda_{max}$ of 560 nm) as a light filter.
Figure 3D:
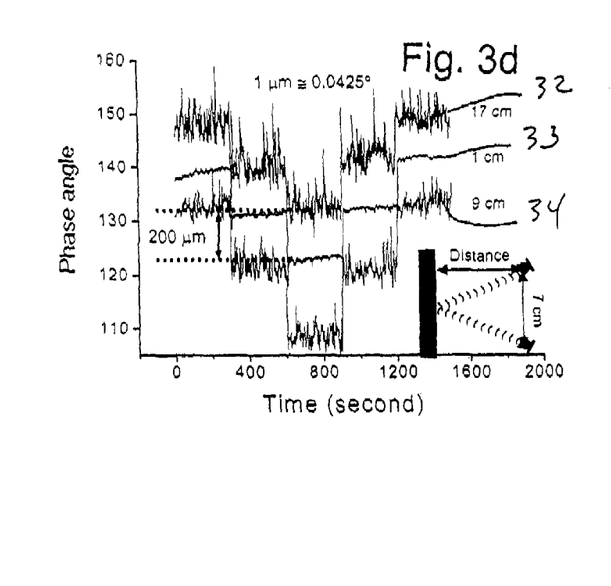
FIG. 3d is a graph of phase angle as a function of time for a test sample in the reflection mode at the sample-transducer distances of 1 cm, 9 cm and 17 cm, respectively.

The validity of the method of the present invention is demonstrated in both transmission and reflection modes. In the transmission mode, the sample is placed in a 2 cm diameter transparent glass tube 20 between two transducers (FIG. 2). The transducers 13a, 14a, and the tube 20 form a 7 cm long resonance tube that greatly reduces noise to less than 0.2° phase change. A mixture of phthalocyanine and NaCl powder at mass ratio of 5% is ground and pressed to form a pellet. The mixture has a strong absorbance at 600 nm and a weak absorbance at 500 nm. As a result, in FIG. 3a, illuminating the pellet with 600 nm (curve 26) and 500 nm (curve 27) lights using according interference filters for five (5) minutes leads to phase changes of 45° and 10°, respectively. In the reflection mode, the distance between the centers of two transducers is 7 cm, and that from the center of one transducer to sample is 1 cm. In FIG. 3b, the illumination of a p-type silicon wafer in this mode using the 600 nm and 500 nm interference filters generates the similar magnitude of phase changes (curves 28 and 29, respectively) as a result of similar absorbance at these wavelengths.

Principally the phase change in reverse photoacoustic effect is a result of the light-induced temperature increase and the thermal expansions of the sample and nearby medium. In the continuous illumination condition, the sample temperature T at the sample-medium interface can be approximated by $$T \approx \frac{H_{abs}}{M_{th}} = \frac{I_0(1 - e^{-\varepsilon l})}{\rho C \mu} \quad (1)$$

where $H_{abs} \approx I_0 A(1-e^{-\beta\mu})$ is the amount of heat generated from light energy, $M_{th}=\rho C\mu A$ is the thermal mass of the illuminated sample region, A is the illuminated area, $I_0$ is the incident light intensity, $\varepsilon$ is the optical absorption coefficient, $\mu$ is the thermal diffusion length, l is the light absorption distance, $\rho$ and C are the density and specific heat of the sample. The sample displacement can be estimated by assuming a free front surface and a fixed back surface, thus the front surface expands a distance equal to the total sample expansion. In addition, the temperature of gas adjacent to the front surface will increase via convection, and the subsequent expansion can be modeled as ideal gas. Thus, $$d_{total} = d_{solid} + d_{gas} \quad (2)$$

$$\approx \alpha \frac{H_{abs}}{M_{th}} \mu + \frac{1}{3} L\beta \cdot \Delta T$$

$$= \alpha \frac{I_0(1 - e^{-\varepsilon l})}{\rho C} + \frac{1}{3} L\beta \cdot \left[\frac{I_0(1 - e^{-\varepsilon l})}{\rho C \mu} - T_0\right]$$

where $\alpha$ is thermal diffusivity, L is the thickness of gas layer, $\beta$ is the volume expansion coefficient of gas, $\Delta T$ is the temperature difference before ($T_0$) and after (T) illumination. If the transducer emits a harmonic ultrasonic wave at the angular frequency of $f_0$, the phase change detected by the receiver is given by $$\phi = \frac{2\pi}{\lambda} \cdot d_{total} = \frac{2\pi}{v} \cdot d_{total} \quad (3)$$

where $\lambda$ is the wavelength of the ultrasonic wave, and v is the sound speed that is 343 m/s at 20° C. The phase changes keep constant as long as the sample to transducer distances (D) satisfy $$D = n\lambda + d_{total} \quad (4)$$

where n is an integer. This is the basis for remote detection of phase change using reverse photoacoustic effect.

In addition to sample displacement due to local temperature change caused by the absorption of electromagnetic waves, the medium (fluid) around the sample may also experience temperature change due to contact with the sample affecting the velocity of the reflected acoustic waves.

In the transmission mode, the local temperature of the object affects the sound velocity. Absorption of the optical waves causes the molecules to vibrate and dissipate the energy as temperature rise. Acoustic wave velocity increases slightly with temperature rise and results in a phase difference.

As illustrated in FIG. 3, the surface temperature (curve 30) of a glass filter (50×50×2 cm) with strong light absorbing ability and the phase angle (curve 31) of a reflecting ultrasonic wave is measured simultaneously using a dye solution ($\lambda_{max}$ at 560 nm) as filter. The temperature can be measured with an Omega 871A digital thermometer by attaching temperature probe to the back of glass filter. The temperature change is coincident with the phase change during the illumination; the phase change and temperature increase are 70° and 50° C., respectively. The equivalent displacement is used to quantitatively relate thermal expansion to phase change. The displacements of the glass filter relative to transducers within the length of a wavelength (8.3 mm at sound speed of 343 m/s for 40 kHz ultrasonic wave) lead to linear phase changes in the reflection mode, where 0.0425° phase change is equivalent to 1 μm displacement. This ratio does not change much when the sample-transducer distance increases from 1 cm to 17 cm. as shown by curves 32, 33 and 34 in FIG. 3d. The displacement of the glass slide is then calculated as 650 μm from the phase changes described above. On the other hand, even if the backside of glass filter is fixed, the thermal expansion is responsible for 6.2 μm of displacement (thermal expansion coefficient of $10^{-5}$/K). As the temperature increase of the glass filter heats the nearby medium, the detected phase change contains the contribution from the thermal expansion of fluid next to the surface.

The magnitude of phase change depends strongly on the light intensity and sample absorbance. The interference filters have narrow wavelength band and high spectral resolution. However, the filtered light is insufficient to generate reliable phase changes for some thin film samples. Meanwhile the optical properties of a given filter are fixed and offer no flexibility for adjustment. We have used a series of dye solutions as inverse filters: the reduction of spectral resolution is compensated with high flux light energy, large phase change and adjustable absorbance. Such a filter array produces a low-resolution spectrum of phase changes that depend on the specific optical and thermal properties of sample. An unknown sample can be identified remotely by comparing its response pattern to a reference spectrum collected on the same array. Such a filter array may include every possible candidate and make the recognition much simpler.

Figure 4A:
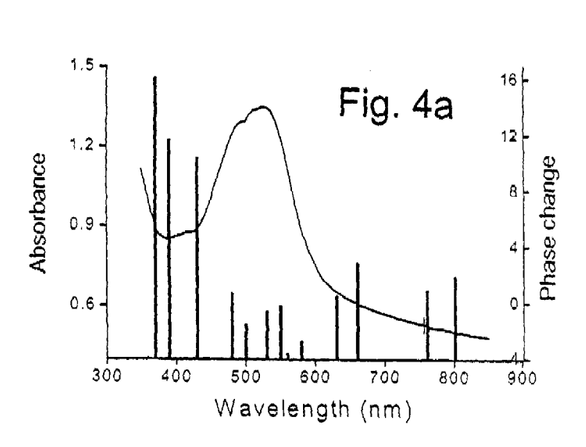
FIG. 4a-4c show phase spectra and phase angle change as a function of wavelength spectra obtained in the transmission mode using an array of filters, for three respective samples.
Figure 4B:
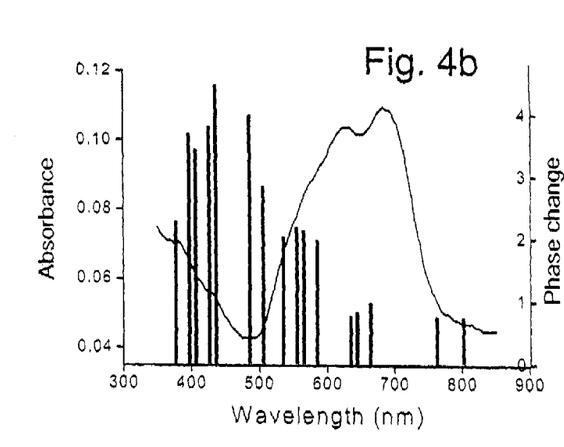
Figure 4C:
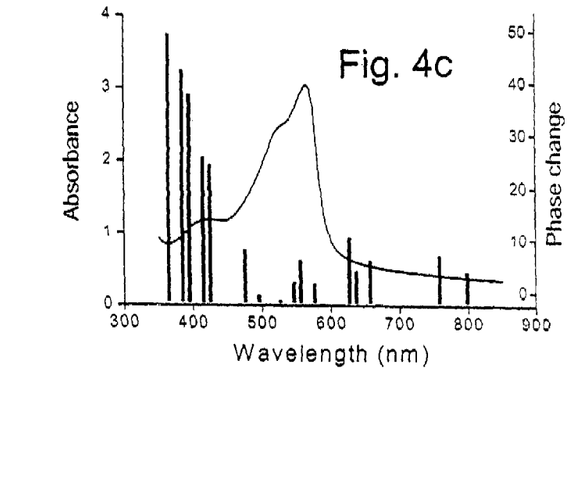
Figure 4D:
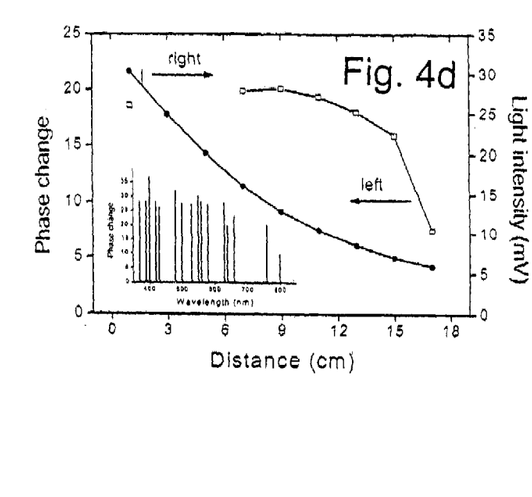
FIG. 4d shows the relation between the phase changes obtained for varying sample-transducer distances using the dye solution filter ($\lambda_{max}$ of 560 nm)

A filter array can be simulated with 16 ethanol solutions of different dyes with $\lambda_{max}$ from 370 nm to 800 nm. Each filter solution allows only a certain amount of light to pass. If the absorbance peak of a sample is overlapped with that of a dye filter, the phase change of the sample is minimal. This is because most of the energy that can be adsorbed by the sample has been adsorbed by the dye filter. In this way we have established the response spectra of several samples in the reflection mode at the sample-transducer distance of 1 cm. The phase changes are plotted as a function of the maximum absorbance peak of each filter solution. FIGS. 4a-4d show the representative phase change spectra of two glass slides covered with thin films of rhodamine 6G and hexamethylindodicarbocyanine iodide (HIDC), a red plastic film and a glass filter. The phase change of the first slide ($\lambda_{max}$ of 530 nm) is minimal when the filter solution of rhodamine 6G is used (FIG. 4a); the HIDC covered slide has small absorbance, but also shows a detectable phase change that is inverse to the optical absorbance (FIG. 4b). The illumination is three minutes rather than five minutes as in other tests, and the red plastic film ($\lambda_{max}$ of 560 nm) shows the largest phase change (40°) as the result of strong absorbance and large thermal expansion coefficient (FIG. 4c), the phase change is roughly inverse to the absorbance of the film; the glass filter shows a large phase change of 25-30° due to its large absorbance (FIG. 4d inset).

Ultrasonic techniques have been used to locate remote objects in various systems, where the detection range can be over several hundred meters. Similarly, the response of phase change in our tests has not been limited to one particular distance. FIG. 4d shows that the phase change of a glass filter as a function of the distance between the sample and the transducer using a dye solution with $\lambda_{max}$ of 560 nm as filter in the reflection mode. The phase changes after illumination for five minutes are around 20° at distances from 1 cm to 10 cm and drop to 7.5° at a distance of 17 cm. The light intensity at different distances is then measured by using a silicon photo-detector (Spectra-physics, Oriel Instruments) and shown in the same FIG. 4d, where an exponentially decreasing tendency is evident. Because the phase angle is independent of the sample-transducer distance as long as the distance is an integer multiple of the wavelength (FIG. 4d), the different decay behaviors of phase change and light intensity are related to the different illumination states of the glass filter and the photodetector. Geometrically, the photodetector has a small detection aperture (diameter of 3 mm) and the glass filter has an edge length of 50 mm. The size of the illuminated area is dependent on the distance: when the distance is between 1 cm and 10 cm, most of the light energy is transferred to the glass filter, which has uniform temperature across the whole surface as the heat transfer occurs fast; when the distance is over 12 cm, some light energy is not used in heating the glass filter, and the phase change is smaller due to the reduced light energy. Furthermore, the uniform temperature distribution on the glass filter has been confirmed by measuring the surface temperature of illuminated and non-illuminated regions. Based on such analysis, the current systems are projected to be able to detect photo-induced phase change at a distance over ten meters in an engineered design where the light intensity is increased.

It is also possible to use various lasers as light sources for increased light intensity. It should be noted that the signal to noise ratio depends on the area of illumination by the acoustic beam and the electromagnetic beam. It is possible to scan the laser beam or focused light beam such that the area illuminated by the electromagnetic wave is almost same as the area of reflection or transmission of the acoustic beam.

It is possible to use this technique for noninvasive detection of physiologically relevant analytes such as glucose. This can be accomplished using reflection or transmission modes of operation. Glucose has many unique absorption peaks in the near and far infrared region of the electromagnetic spectrum.

Another possible application will be superimposing chemical signatures to an ultrasound image. An ultrasound image is basically due to the reflection of ultrasonic waves from objects of different densities. Using reverse photo acoustic technique its possible to add chemical signatures to ultrasonic images by illuminating the object with different electromagnetic waves.

An ultrasonic reading machine based on the reverse photoacoustic effect can also be used to develop both black-and-white and colored visual features using ultrasonic transducers 13, 14, a light source 11, a group of interchangeable filters 12 and the electronic control 21 as shown in FIGS. 1 and 2. The absorption of white or filtered light will increase the local temperature of a feature, which changes the phase angle of a reflected or transmitted ultrasonic wave. The high sensitivity of the phase related distance measurement enables the reliable and fast recognition of black features using white illumination or colorful features using a combination of filtered lights. The minimum readable feature size can be reduced by passing the ultrasonic beam through a narrow aperture produced on a high impedance plate. Compared with its available optical counterparts, the ultrasonic reading machine offers numerous advantages in reading the features on a non-planar support or at non-touchable distances, such as those attached on solid stands.

Figure 5A:
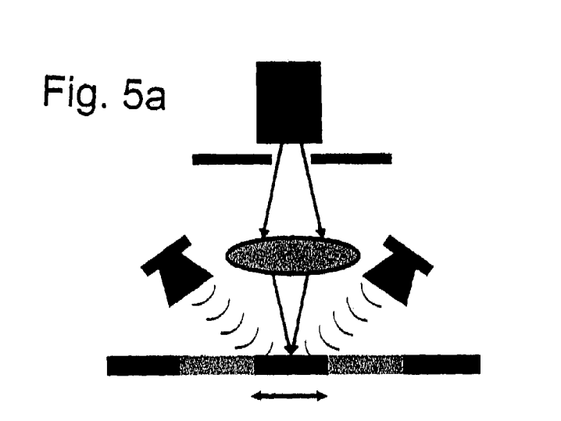
FIG. 5a shows schematic diagram for an apparatus for sensing light, dark and color.

An ultrasonic-based method for the recognition of visual features can also be based on the reverse photoacoustic effect. The adsorption of light illumination increases the local temperature of a surface (i.e. paper) and a nearby medium, which changes the phase angle of any reflecting or transmitting ultrasonic wave (FIG. 5a). Sample expansion can be estimated by assuming a free front surface and a fixed back one, and the front surface expands a distance equal to the total sample expansion. The temperature of gas adjacent to the front surface will increase via convection. If the gas expansion follows ideal gas behavior, the total thermal expansion can be modeled as:

$$d_{total} = d_{solid} + d_{gas}$$
$$\approx \alpha \frac{H_{abs}}{M_{th}} \mu + \frac{1}{3} L\beta \cdot \Delta T$$
$$= \alpha \frac{I_0(1-e^{-\epsilon l})}{\rho C} + \frac{1}{3} L\beta \cdot \left[\frac{I_0(1-e^{-\epsilon l})}{\rho C \mu} - T_0\right]$$

where $H_{abs} \approx I_0 A(1-e^{-\beta\mu})$ is the amount of heat generated from light energy, $M_{th} = \rho C \mu A$ is the thermal mass of the illuminated sample region, A is the illuminated area, $I_0$ is the incident light intensity, $\epsilon$ is the optical absorption coefficient, $\mu$ is the thermal diffusion length, l is the light absorption distance, $\rho$ and C are the density and specific heat of the feature, $\alpha$ is thermal diffusivity, L is the thickness of gas layer, $\beta$ is volume expansion coefficient of gas, $\Delta T$ is the temperature difference before ($T_0$) and after (T) illumination. The method is capable of producing sufficient phase change to discriminate black feature and colorful features from white background. The phase change occurs fast upon illumination and the ultrasonic beam can be narrowed to increase the spatial resolution of recognition. If combined with an artificial intelligence system for data processing, the method will be an important alternate and addition for an optically-based reading machine.

A controlled light source 11, 11a as described in relation to FIGS. 1 and 2, can be used for illumination. The intensity of the white light is attenuated to achieve appropriate phase change. A series of interference filters 12, 12a that allow light within a narrow wavelength band to pass (Melles Griot) are used to select the wavelength of the light reaching the sample 16. Two types of ultrasonic transducers 13, 14 with intrinsic frequencies at 40 kHz and 93 kHz (International Transducers) are used in the experiment. These transducers have a small divergence angle 22 of ten degrees from a shortest direct path of travel 18 between the transducers 13, 14. These form the directional beams that are required to reach a remote target. Two transducers 13, 14 are fixed at a certain distance to each other, along the path 18, and are properly orientated to maximize the received transmitting or reflecting signal. An electronic control 21, 21a is again used to drive the vibration of one transducer/transmitter 13, 13a at its intrinsic frequencies and collect ultrasonic signals from another transducer/receiver 14, 14a. In one test, both black features and colored features are printed onto white paper using laser printers. The paper is then fixed onto a metal plate or a plastic supporting plate in the reflection mode, or placed in a transparent plastic tube in the transmission mode.

Figure 5B:
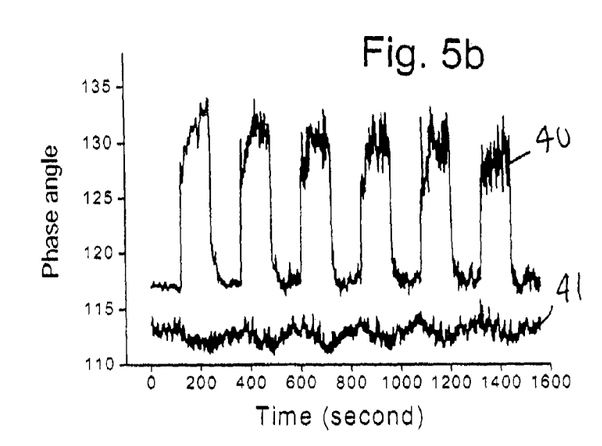
FIG. 5b is a graph of phase angle as a function of time for black and white features printed on white paper in the reflection mode using white illumination light.
Figure 5C:
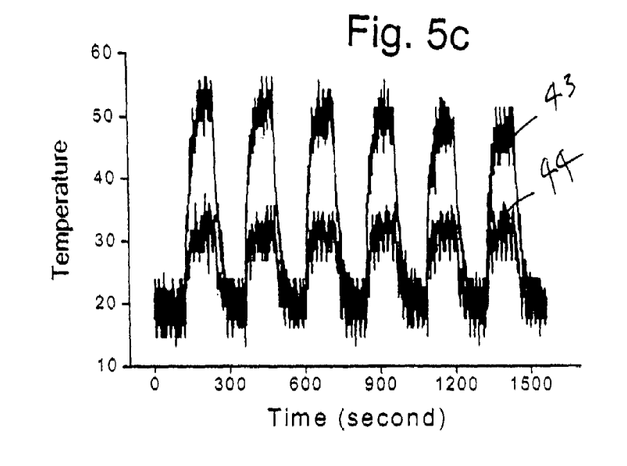
FIG. 5c is a graph of temperature as a function of time for black and white features printed on white paper in the reflection mode using white illumination light.
Figure 5D:
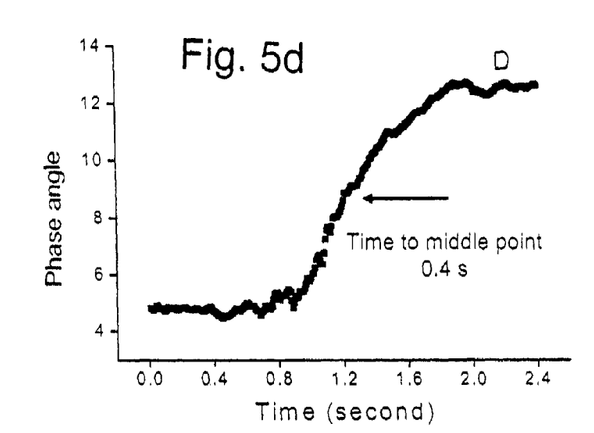
FIG. 5d is a graph of phase angle change vs. time that shows a fast phase response with the time to the middle of phase change of around 0.4 seconds.

The anticipated phase changes of black features and white features are confirmed in the reflection mode using white illumination and 40 kHz transducers at the emitter-receiver distance of five cm and the transducer-feature distance of five cm. FIG. 5b shows the responses of phase angles collected on the black feature (curve 40) and white feature (curve 41) (the paper itself) in a series cycles of light exposure. Statistically, the phase change difference is significant to discriminate the black feature from the white one. The phase angle changes ten degrees in the first two seconds for the black feature and reaches a saturated value in 30 seconds. By comparison, only small phase angle fluctuations exist for the white feature, which could be related to the light absorption by supporting plate or paper tissue. To confirm whether the phase change is accompanied by the temperature increase of the paper, the temperatures of the features are measured simultaneously using an Omega 871A digital thermometer. FIG. 5c indicates that the temperature change is coincident with the phase change during the illumination: the temperature increases are 33° and 10° C. for black and white features, respectively (curves 43 and 44). The photo-induced temperature increase and subsequent phase change occur in a fast fashion, and satisfy one basic requirement as a feasible reading machine. FIG. 5d shows that the time needed to reach the middle point of total phase change is 0.4 seconds without intentionally optimizing conditions such as the light intensity and the background supporting plate. Thus, the reading machine is capable of recognizing black features from white ones in less than one second assuming the equal amount of time to collecting the base line and identifying the phase change.

Figure 6A:
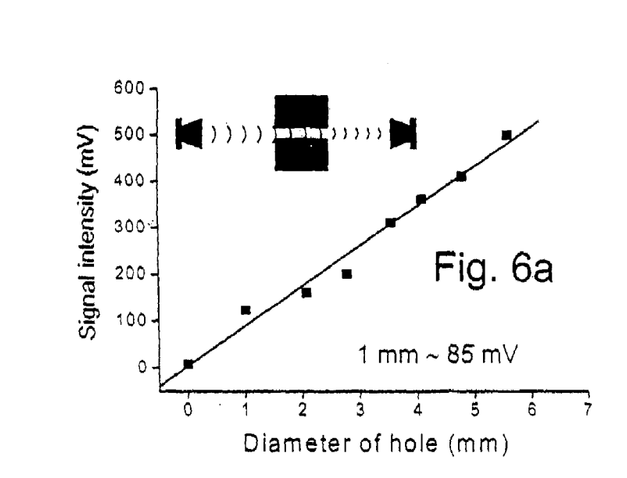
FIG. 6a is a graph of signal intensity vs. aperture diameter in a transmission mode.
Figure 6B:
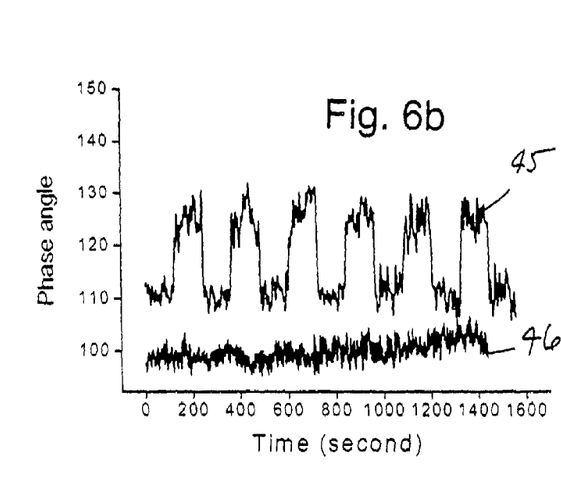
FIG. 6b is a graph of phase angle vs. time for black features and white features in the reflection mode using a 1 mm diameter aperture.

Another important factor of a reading machine is the minimal recognizable feature size that is dependent on the diameter of the ultrasonic beam. Although the size of the ultrasonic beam is larger than the transducer diameter (25 mm), the beam size can be narrowed by using a small aperture drilled on a 5 mm thick polycarbonate plate. The large difference in acoustic impedances (defined as the product of the material density and the sound speed in the material) of polycarbonate (2690 N·s/m³ at 20° C.) and air (413 N·s/m³ at 20° C.) will effectively reduce the beam size. FIG. 6a shows that at the constant driven voltage of 5 V and transmitter-receiver distance of five mm, the vibration amplitudes of the received ultrasonic wave (measured in millivolts) after passing through various apertures change with aperture diameters ranging from 1 to 6 mm. The amplitude obtained using the smallest aperture (1.02 mm) is close to 100 mV, which is sufficient to monitor the waveform and phase angle of ultrasonic wave. Subsequently, the polycarbonate plate is made into an ultrasonic shield with a 1 mm aperture to narrow the ultrasonic beam, and the shield is used to detect the phase change of black and white features in the reflection mode with controlled exposure to white illumination. The observed phase change on the black feature (curve 45) has the same order of magnitude as that collected without aperture, and is larger than that observed on the white feature (curve 46)(FIG. 6b). Thus, the aperture-size independent phase change offers an additional flexibility where the detection area can be as small as aperture size without losing the phase information.

Figure 6C:
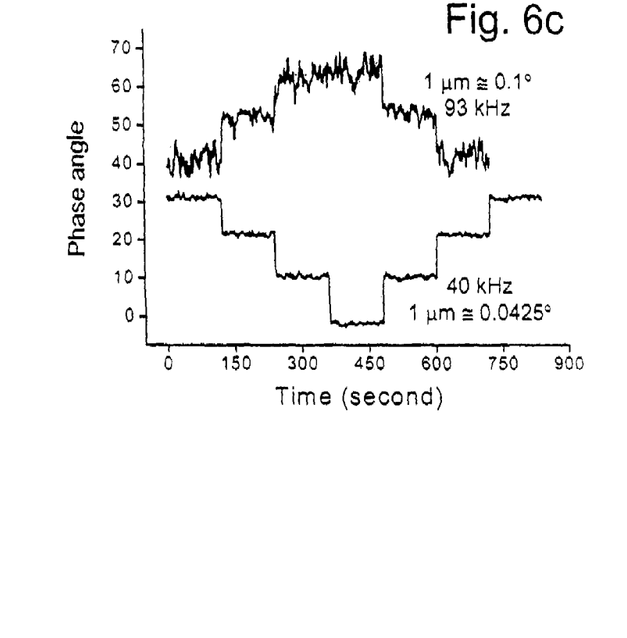
FIG. 6c is a graph of phase angle vs. distance for 40 kHz transducers vs. 93 kHz transducers.

Phase angle sensitivity based detection strongly depends on the intrinsic frequency of the ultrasonic transducers used in the experiment. A higher frequency ultrasonic wave has shorter wavelength and thus is more sensitive to the small deformation or displacement of feature surface. FIG. 6c shows the relationship between the phase change and the sample physical displacement measured in the reflection mode for two 40 kHz transducers and two 93 kHz transducers at the transducer-transducer distance of 5 cm and the transducer to surface distance of 4 cm. The wavelengths of the 40 kHz and 93 kHz transducers are 8.6 mm and 3.7 at the sound speed of 343 m/s. Based on a simple calculation, 1 μm sample displacement corresponds to 0.0425° phase change for the 40 kHz transducer and 0.1° phase change for the 93 kHz one. Thus the sensitivity of 93 kHz transducer is two times higher than that of 40 kHz transducer. Although the noise level increases also for the higher frequency one, the problem is alleviated in the transmission mode using an isolating chamber to reduce surrounding perturbation. We believe such a chamber does not significantly degrade the usability as a reading machine.

Figure 6D:
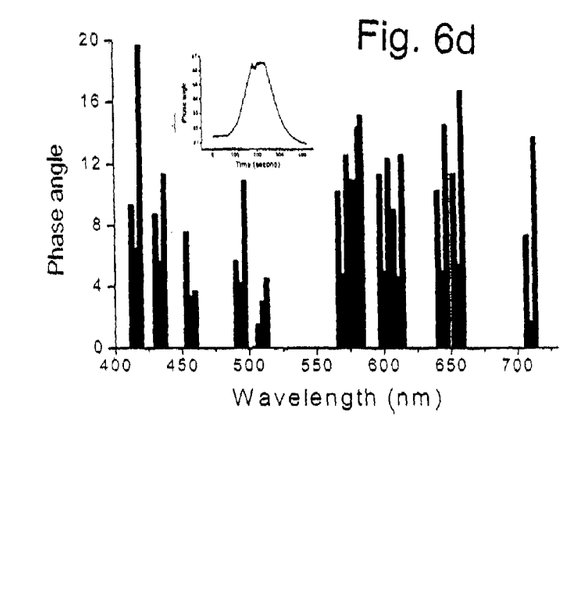
FIG. 6d is graph of phase angle changes of red, green and blue features on white paper in the reflection mode as a function of wavelength transmitted through different interference filters.

The ultrasonic reading machine can be used to recognize a colored feature if an appropriated filter array is used to select the illumination wavelength. For this purpose, a series of interference filters are used and the detection is performed using 93 kHz transducers in the transmission mode in order to increase the sensitivity and reduce the noise. A colored feature printed on white paper using a laser printer was placed inside of a 25 mm diameter transparent plastic tube, and the two transducers are placed at the two terminals with a distance of 45 mm to form a seamless chamber. The heat generated by the colored feature will heat up the contained air, and consequently will change the phase angle of any ultrasonic standing wave established inside the chamber. FIG. 6d inset shows a typical curve of phase change collected on a blue feature using a 644 nm filter with illumination during of two minutes. The air-mediated phase change is further confirmed from the near equilateral relationship shown in the phase change vs. time curve. Ultimately the phase changes of the blue feature, a red feature and a green feature are collected under the same condition using an array of different filters as shown in FIG. 5d. Although the discrete diagrams cannot reflect the exact absorption properties of each feature, because the energy flux from the light source at each wavelength is different, the ratio and shape of transmission curve of each filter are different, the collective phase changes obtained using the same filter array can be used to recognize different colors providing a database of phase change of different colored features based on the same light source and filter group.

Figure 7:
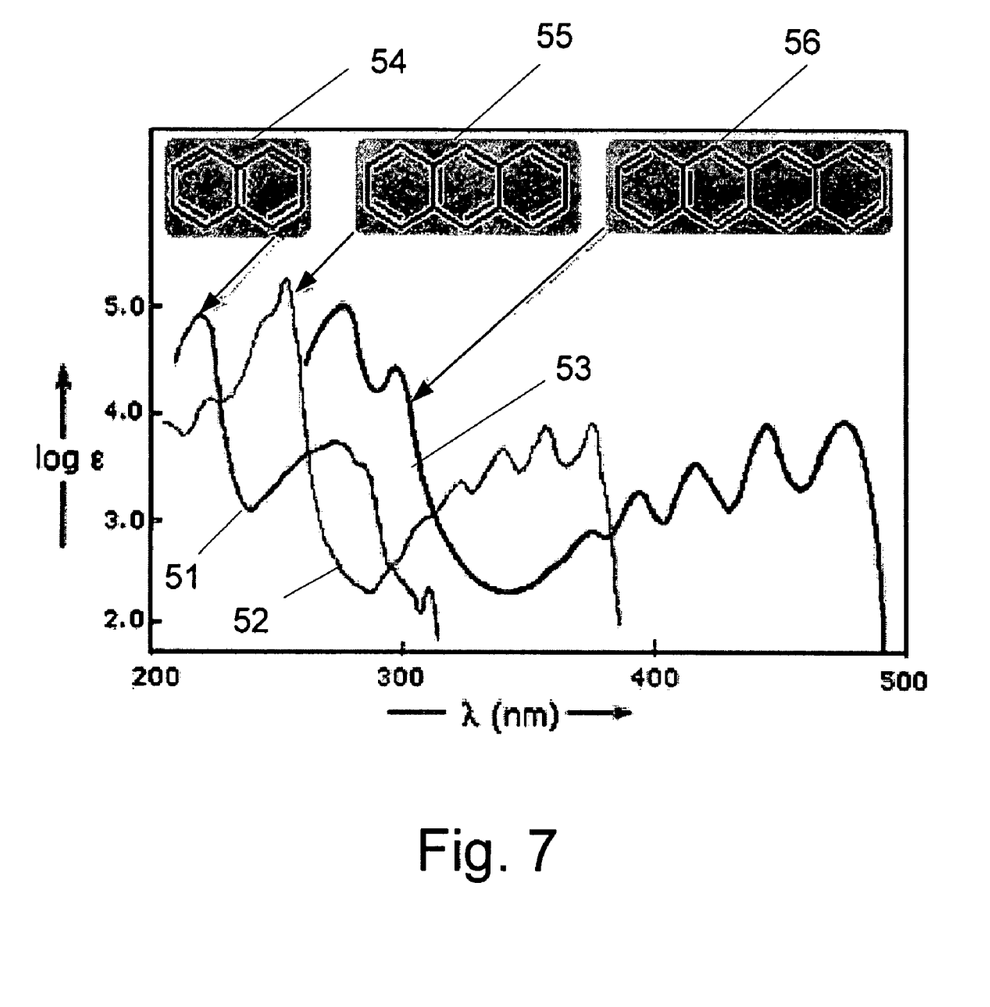
FIG. 7 is a graph of intensity vs. wavelength for three different samples.

In another embodiment, which is the preferred embodiment in this application, for operation at nanoscale, different energy vs. wavelength spectra or graphical data 51, 52, 53 are displayed for different molecular compositions represented by chemical composition graphs 54, 55 and 56, respectively. This shows that differences in molecules will produce different optically sensed energy levels at different wavelengths of excitation.

Figure 8:
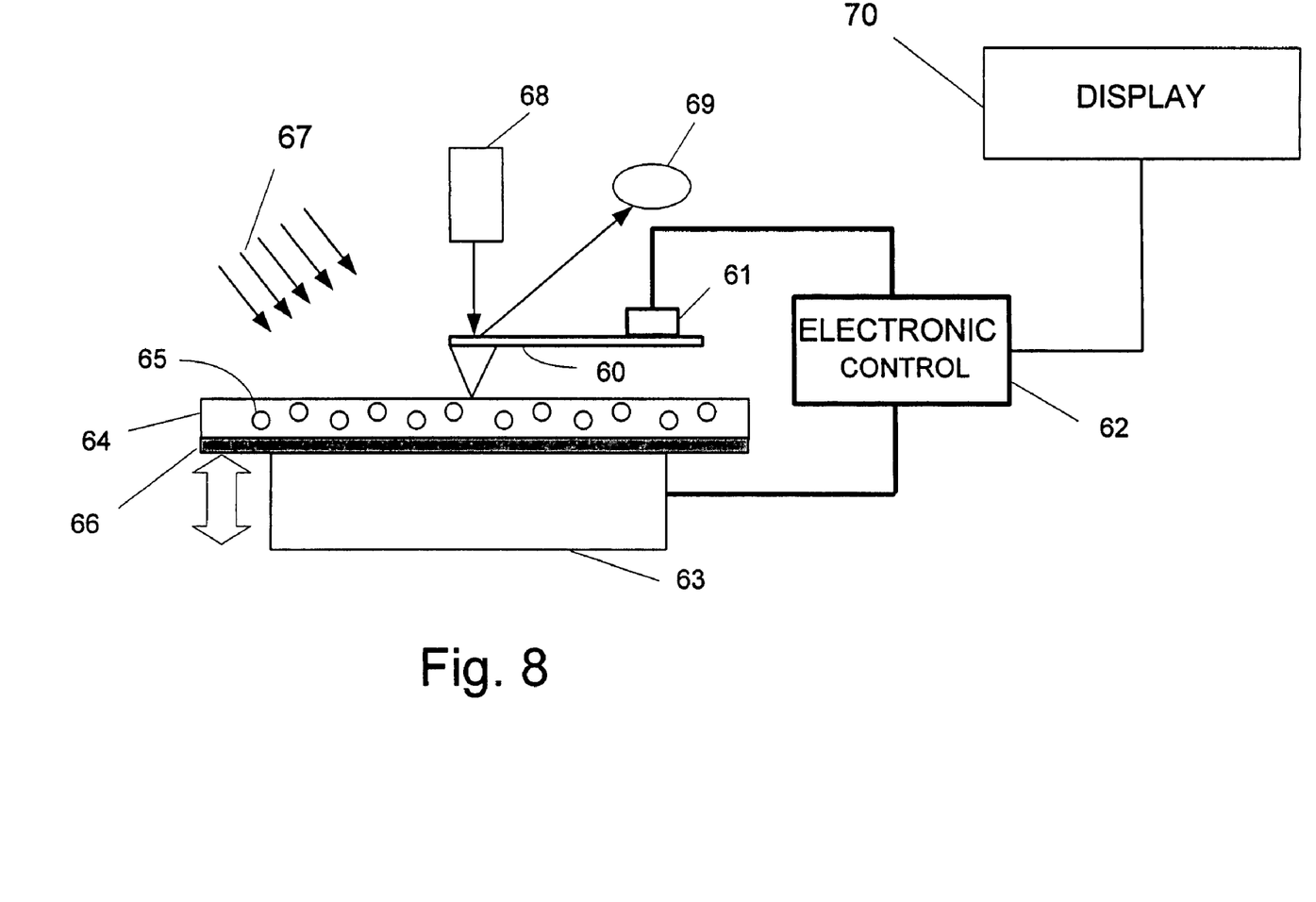
FIG. 8 is a block diagram of an apparatus for identifying molecular species at nanoscale.

An ultrasonic method, near-field acoustic holography has been developed recently to image the embedded nanoparticles using ultrasonic holography and the reverse photoacoustic effect. The apparatus for practicing the method is illustrated in FIG. 8. In this figure, a microcantilever 60 is provided with an acoustic signal through a transducer 61 and a circuit including a lock-in amplifier 62, which also controls generation of acoustic signals through a base 63. A polymeric sample 64 with molecules 65 of nanoscale and of different colors is placed on a table 66 than can be shaken or vibrated, as represented by the double-headed arrow. A source of illumination energy 67 provides illumination radiation to the sample 64 from above. A source of laser light 68 is provided at a first position above the microcantilever 60 and this radiation is reflected and detected at a second position by a detector 69 to detect movement of the tip of the microcantilever 60.

In the method of this invention at nanoscale, the light source 65 provides infrared (IR) radiation at different wavelengths for local heating of molecules in the sample, which will cause a change of phase in the acoustic wave being transmitted through local regions in the sample. A high frequency (~100's of KHz) acoustic wave is launched from the base 63 through the bottom of the specimen 64, while another acoustic wave is applied through the transducer 61, albeit at a slightly different frequency. The interferences of these two waves would nominally form so-called "beat frequency" which is monitored at a tip of the cantilever 60 by sensor 69. The tip acts as an antenna for both phase and amplitude of the beat frequency. As the specimen acoustic wave gets perturbed by subsurface (and surface) features, especially its phase, the local acoustic interference is very effectively monitored by sensing movement of the AFM tip using the sensor 69. Thus, within the near-field range (which enjoys superb lateral and vertical resolution), the acoustic wave (which is non-destructive and sensitive to mechanical/elastic variation in its "path") is fully analyzed, point-by-point, across the sample 64, by sensing the acoustic antenna at the tip of the cantilever 60 in terms of phase and amplitude. Thus, as the specimen 64 is scanned across, a pictorial representation of the acoustic wave's movement is fully recorded and displayed on display 70, to offer "quantitative" account of internal microstructure of the specimen 64. In the above example, the arrangement has been used to detect different colored molecules. It is therefore possible to detect chemical composition of such molecules based on comparison with suitable chemical spectra.

Figure 9:
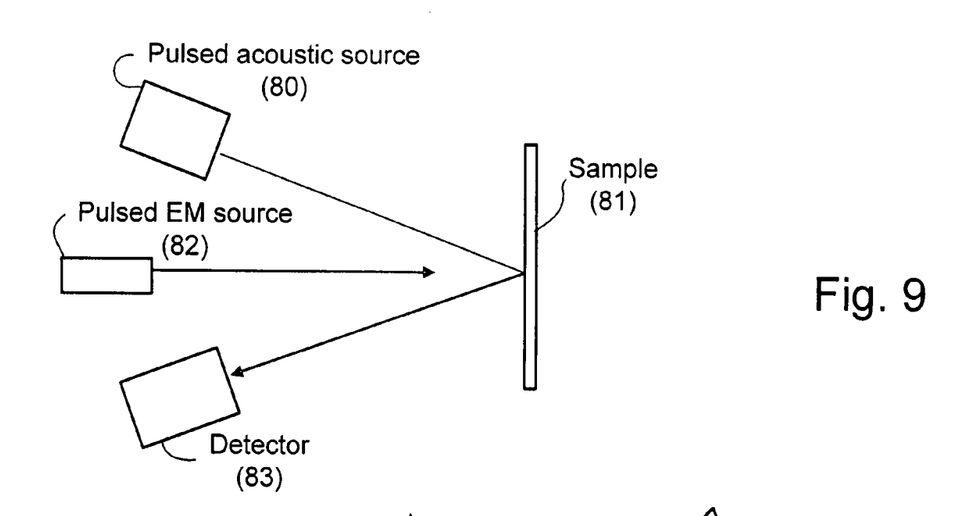
FIG. 9 is block diagram illustrating an alternative method and device for practicing the present invention.
Figure 10:
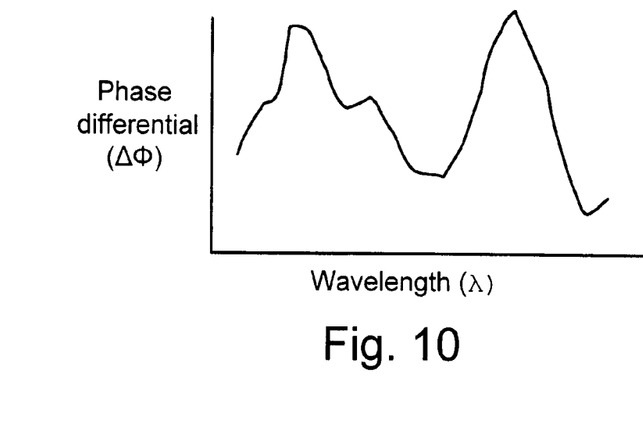
FIG. 10 is a graph of phase differential of illuminated and non-illuminated acoustic pulse phases as a function of wavelength ($\lambda$) of signal impinging on a surface of a sample.

FIG. 9 illustrates a pulsed mode of operation for the device of the present invention. In the pulsed mode of operation, an acoustic wave pulse is transmitted from a source 80 to a surface of a sample 81, is reflected, and is then detected by detector 83. The phase difference between the acoustic pulse transmitted from the source 80 and detected at the detector 83 is measured and stored in a memory (not shown). A second acoustic pulse is transmitted from a source 80 to a surface of a sample 81, is reflected, and is then detected by detector 83 while illuminating the sample with an electromagnetic radiation of a given wavelength from illumination source 82. The phase difference between the acoustic pulse transmitted from the source 80 and detected at the detector 83 during illumination is measured and stored in the memory (not shown). The phase differences in the unilluminated cycle and the illuminated cycle can be recalled from memory and calculated as a phase differential. This phase differential is illustrated in FIG. 10 as a function of different exposing wavelengths (λ) to show the electromagnetic absorption characteristics of the sample surface. This differential mode of operation is advantageous in that it eliminates the interference due to variation in the intervening medium during operation of the device. It is expected that the vapors of the sample in the intervening medium are small. All the surfaces act as a collector for sample vapor and adsorbs with a concentration that can be orders of magnitude higher than that in the air. Therefore, the pulsed mode offer a method for collecting chemical signatures in a standoff fashion when the intervening medium is changing faster than the time required for collecting the chemical signature.

The pulsed mode of operation can be practiced can also be practiced in a transmission mode of operation where the acoustic source and the detector are on opposite sides of the sample. The acoustic source and the acoustic detector can be in intimate contact with the sample.

This completes the detailed description of the preferred embodiments of the invention. It will be understood by those of ordinary skill in the art that various modifications can be made to the details without departing from the scope and spirit of the invention as defined by the following claims.

We claim:

1. A method for identifying a sample, the method comprising:
   exposing the sample to electromagnetic radiation of varying wavelengths to cause absorption of electromagnetic radiation in the sample;
   during said exposure, transmitting an acoustic wave onto the sample from one position and receiving the acoustic wave at another position;
   detecting a change of phase in the acoustic wave induced by the absorption of the electromagnetic radiation of varying wavelengths; and
   analyzing the change of phase for the electromagnetic radiation of varying wavelengths to identify the sample.

2. The method of claim 1, wherein the sample is identified as to chemical composition.

3. The method of claim 1, wherein the sample is identified as to a character of being black or white.

4. The method of claim 1, wherein the sample is identified as to a character of being absorbing or non-absorbing.

5. The method of claim 1, wherein portions of the sample are identified as to color.

6. The method of claim 1, wherein an acoustic transmitter and an acoustic receiver are opposite each other, but offset from the sample by a distance so as to form an angle of incidence to the sample and an angle of reflection from the sample, and wherein the acoustic wave is transmitted to the sample from the acoustic transmitter and then reflected in a reflection mode to the acoustic receiver.

7. The method of claim 6, wherein the angle of incidence is equal to the angle of reflection and is approximately eighty degrees.

8. The method of claim 1, wherein an acoustic transmitter and an acoustic receiver are directly opposite each other; wherein the sample is midway between the acoustic transmitter and the acoustic receiver, and wherein the acoustic wave is transmitted in a transmission mode through the sample from the acoustic transmitter to the acoustic receiver.

9. The method of claim 1, wherein illuminating the sample with light of varying wavelengths further comprises generating a beam of light and passing said beam of light through a plurality of filters before the light contacts the sample.

10. The method in claim 1, wherein the sample is a human body part, and wherein the acoustic signal passes to or is reflected to an acoustic detector from the human body part, wherein the human body part is radiated with electromagnetic waves of varying frequencies for producing the absorption spectra of physiologically relevant materials such as glucose.

11. The method in claim 1, wherein the method is carried out to sense points of the sample within nanoscale dimensions, and wherein individual molecules are identified.

12. An apparatus for identifying a sample, the apparatus comprising:
   a controllable source of electromagnetic radiation for exposing the sample to electromagnetic radiation of varying wavelengths to cause absorption of electromagnetic radiation in the sample
   a transmitter for transmitting an acoustic wave onto the sample from a first position;
   a receiver for receiving the acoustic wave at a second position relative to the sample and converting the acoustic wave to an electronic signal;
   an electronic circuit having a first portion for receiving the electronic signals and detecting a change of phase in the acoustic wave induced by the absorption of the electromagnetic radiation and corresponding to respective ones of the varying wavelengths of varying wavelengths; and
   the electronic circuit having a second portion for outputting the change of phase in the acoustic wave for the electromagnetic radiation of varying wavelengths to allow identification of the sample.

13. The apparatus of claim 12, wherein the sample is identified as to chemical composition.

14. The apparatus of claim 12, wherein the sample is identified as to a character of being black or white.

15. The apparatus of claim 12, wherein portions of the sample are identified as to color.

16. The apparatus of claim 12, wherein the electromagnetic radiation is selected from a group consisting of ultraviolet, optical, infrared, microwave, millimeter waves, and terahertz waves.

17. The apparatus of claim 12, wherein the transmitter and receiver are opposite each other but offset from the sample by a distance so as to form an angle of incidence to the sample and an angle of reflection from the sample, and wherein the acoustic wave is transmitted to the sample from the transmitter and then reflected in a reflection mode to the receiver.

18. The apparatus of claim 17, wherein the angle of incidence is equal to the angle of reflection and is approximately eighty degrees.

19. The apparatus of claim 17, wherein the transmitter and receiver are directly opposite each other; wherein the sample is midway between the transmitter and receiver, and wherein the acoustic wave is transmitted in a transmission mode through the sample from the transmitter to the receiver.

20. The apparatus of claim 17, wherein the controllable source of electromagnetic radiation for exposing the sample to electromagnetic radiation of varying wavelengths further comprises a light source for generating a beam of light and a plurality of filters through which the light is passed before the light contacts the sample.

21. An apparatus for identifying molecules in a sample, the apparatus comprising:

a controllable source of electromagnetic radiation for exposing the sample to electromagnetic radiation of varying wavelengths;

a transmitter for transmitting an acoustic wave through the sample;

a microcantilever with a tip for positioning at varying positions on the sample;

a sensor for sensing vibratory movement of the microcantilever tip in response to a phase change in frequency of the acoustic wave and in response to the wavelength of radiation applied to a region of the sample near the microcantilever tip;

an electronic circuit having a first portion for receiving the electronic signals and detecting a change of phase in the acoustic wave corresponding to respective ones of the varying wavelengths; and the electronic circuit having a second portion for outputting the change of phase for the acoustic wave for the varying wavelengths of electromagnetic radiation to allow identification of at least one of chemical composition and color of the sample.

22. The apparatus of claim 21, wherein the sample is identified as to chemical composition.

23. The apparatus of claim 21, wherein portions of the sample are identified as to color.

24. A method for identifying a sample, the method comprising:

transmitting a first acoustic signal from a source to a sample;

detecting the first acoustic signal at a detector;

determining a first phase difference between the acoustic signal at the source and the acoustic signal at the detector;

transmitting a second acoustic signal from a source to the sample while illuminating the sample with electromagnetic radiation;

detecting the second acoustic signal at the detector;

determining a second phase difference between the second acoustic signal at the source and the second acoustic signal at the detector; and determining a differential between the first phase difference and the second phase difference and in response thereto displaying electromagnetic absorption spectra for the sample.

25. The method of claim 24, wherein the first phase difference is determined without illumination of the sample with electromagnetic radiation.

* * * * *